United States Patent [19]
Knifton et al.

[11] Patent Number: 5,220,078
[45] Date of Patent: Jun. 15, 1993

[54] ONE STEP SYNTHESIS OF METHYL T-BUTYL ETHER FROM T-BUTANOL USING FLUOROPHOSPHORIC ACID-MODIFIED ZEOLITE CATALYSTS

[75] Inventors: John F. Knifton, Austin; John R. Sanderson, Leander, both of Tex.

[73] Assignee: Texaco Chemical Company, White Plains, N.Y.

[21] Appl. No.: 917,885

[22] Filed: Jul. 23, 1992

[51] Int. Cl.$^5$ ............................................. C07C 41/09
[52] U.S. Cl. ..................................... 568/698; 502/65
[58] Field of Search ............................................. 568/698

[56] References Cited

U.S. PATENT DOCUMENTS 2,282,469  5/1942  Frolich ............................. 568/698
5,081,318  1/1992  Knifton ............................. 568/698

Primary Examiner—Howard T. Mars
Attorney, Agent, or Firm—James L. Bailey; Kenneth R. Priem; Cynthia L. Kendrick

[57] ABSTRACT

A method is disclosed wherein t-butanol is reacted with methanol in a reaction zone in one step to provide methyl tert-butyl ether and the improvement in accomplishing the reaction which comprises:

a. Using a catalyst consisting of a crystalline aluminosilicate faujasite Y-type zeolite which has been treated with a fluorophosphoric acid;
b. continuously contacting said t-butanol and methanol in a molar amount of about 0.1 to 10 moles of methanol per mole of t-butanol with said catalyst at a temperature of about 20° C. to about 250° C. and a pressure of about atmospheric to about 1000 psig to obtain the methyl tert-butyl ether product.

8 Claims, No Drawings

ONE STEP SYNTHESIS OF METHYL T-BUTYL ETHER FROM T-BUTANOL USING FLUOROPHOSPHORIC ACID-MODIFIED ZEOLITE CATALYSTS

CROSS-REFERENCE

This application is related to U.S. Pat. Nos. 4,144,138; 4,827,048; 4,822,921; 5,059,725; 5,081,318 and 5,099,072 and to copending application Ser. Nos. 07/796,987; 07/783,015 and 07/803,834, held allowable, and to U.S. application Ser. Nos. 07/494,281; 07/724,071, 07/745,777 and 07/878,121.

This invention concerns an improved process for preparing methyl tertiary-butyl ether (MTBE) by the reaction of tertiary butanol and methanol in the presence of a catalyst comprising fluorophosphoric acid-modified zeolites, particularly certain Y-zeolites. The invention is particularly advantageous in that the reaction takes place in one-step, the catalyst exhibits levels of tert-butanol conversion as high as 87% and total MTBE plus isobutylene selectivity close to quantitative, with the crude product mix separating into an isobutylene-MTBE product-rich phase and a heavier aqueous methanol phase.

BACKGROUND OF THE INVENTION

It is known to those skilled in the art that ethers, including unsymmetrical ethers, may be prepared by reacting an alcohol with another alcohol to form the desired product. The reaction mixture, containing catalyst and/or condensing agent may be separated and further treated to permit attainment of the desired product. Such further treatment commonly includes one or more distillation operations.

Methyl tert-butyl ether is finding increasing use as a blending component in high octane gasoline as the current gasoline additives based on lead and manganese are phased out. Currently all commercial processes for the manufacture of methyl tert-butyl ether are based upon the liquid-phase reaction of isobutylene and methanol (Eq. 1), catalyzed by a cationic ion-exchange resin (see, for example: Hydrocarbon Processing, Oct. 1984, p. 63; Oil and Gas J., Jan. 1, 1979, p. 76; Chem. Economics Handbook-SRI, Sep. 1986, p. 543–7051P). The cationic ion-exchange resins used in MTBE synthesis normally have the sulphonic acid functionality (see: J. Tejero, J. Mol. Catal., 42 (1987) 257; C. Subramamam et al., Can. J. Chem. Eng., 65 (1987) 613).

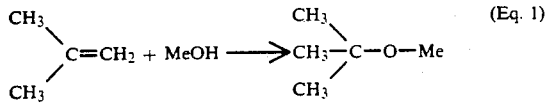

(Eq. 1)

With the expanding use of MTBE as an acceptable gasoline additive, a growing problem is the availability of raw materials. Historically, the critical raw material is isobutylene (Oil and Gas J., Jun. 8, 1987, p. 55). It would be advantageous, therefore, to have a process to make MTBE that does not require isobutylene as a building block. It would be advantageous to have an efficient process for making MTBE by reaction of methanol with tertiary butyl alcohol, since t-butanol (TBA) is readily available commercially through isobutane oxidation.

In U.S. Pat. No. 4,144,138 (1979) to Rao et al., there is disclosed a method for recovering methyl tertiary butyl ether from etherification reaction effluent by azeotropic distillation to recover methanol-ether azeotrope overhead which is water-washed to give pure ether raffinate, the latter being azeotropically distilled to yield ether-methanol overhead which is recycled to wate washing.

The preparation of methyl tert-butyl ether from methyl and tert-butyl alcohols is discussed in S. V. Rozhkov et al., Prevrashch Uglevodorodov, Kislotno-Osnovn. Geterogennykh Katal. Tezisy Dokl. Vses Konf., 1977, 150 (C. A. 92:58165y). Here the TBA and methanol undergo etherification over KU-2 strongly acidic sulfopolystyrene cation-exchangers under mild conditions. This reference contains data on basic parameters of such a process. It is also pointed out that, although a plant for etherification over cation exchangers does not present any major problems, considerations include the fact that recycling large amounts of tert-butyl alcohol and methanol, as well as isobutylene, causes the scheme to be somewhat more expensive. Also, the progress of the reaction over cation exchangers is usually complicated by various adsorption and diffusion factors, by swelling phenomena, and by the variable distribution of the components between the solution and ion-exchanger phase. Furthermore, said acidic cation-exchangers with an organic (polystyrene or polymethacrylate) backbone generally have a very limited stability range with regard to operating temperatures, with temperatures above 120° C. normally leading to irreversible destruction of the resin and loss of catalytic activity.

In U.S. Pat. No. 2,282,469 to Frolich there is disclosed a process for preparing methyl tertiary butyl ether over a catalyst comprising Kieselguhr impregnated with phosphoric acid at a temperature of about 175° F. to 350° F.

Japanese Patent 0007432 teaches the use of zeolites to make dialkyl ethers containing primary or secondary alkyl groups. The zeolites have a porous structure and are represented by:

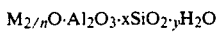

where M is an alkali metal or alkaline earth metal cation or organic base cation, n is the valence of the cation and x and y are variables.

U.S. Pat. No. 4,058,576 to Chang et al. teaches the use of (pentasil-type) aluminosilicate zeolites, such as ZSM-5, having a pore size greater than 5 angstrom units and a silica-to-alumina ratio of at least 12, to convert lower alcohols to a mixture of ethers and olefins.

In U.S. Pat. No. 4,822,921 there is disclosed a method for producing MTBE by reacting tertiary butyl alcohol and methanol in the presence of a catalyst comprising an inert support, such as titania, having a phosphoric acid impregnated thereon.

U.S. Pat. No. 4,827,048 discloses a method for producing MTBE by reacting tertiary butyl alcohol and methanol in the presence of a catalyst comprising a heteropoly acid such as 12-tungstophosphoric acid or 12-molybdophosphoric acid on an inert support, such as titania.

In copending U.S. patent application Ser. No. 07/494,281, there is disclosed a method for preparing methyl tertiary butyl ether by reacting butanol and methanol in the presence of a catalyst comprising a super-acid alumina or a faujasite-type zeolite.

U.S. Pat. No. 5,099,072 discloses the reaction of butanol and methanol in the presence of acidic montmorillonite clay catalysts having certain identifiable physical parameters.

In U.S. Pat. No. 5,081,318 (1992), there is described a one-step method for the synthesis of MTBE from t-butanol using a fluorosulfonic acid-modified zeolite catalyst.

In U.S. Pat. No. 5,059,725 (1991), a one-step synthesis for MTBE is disclosed wherein t-butanol and methanol are reacted over a catalyst comprising ammonium sulfate or sulfuric acid deposited upon a Group IV oxide.

In Ser. No. 07/724,071 a fluorocarbon sulfuric acid polymer on an inert support is disclosed for use as a catalyst for producing MTBE. And, in Ser. No. 07/745,777 there is disclosed the use of a hydrogen fluoride-modified zeolite catalyst for the production of MTBE.

Ser. No. 07/796,987 and 07/783,015, both allowed, claim the one step synthesis of MTBE using a multimetal-modified clay catalyst or a fluorophosphoric acid-modified clay catalyst, respectively.

Ser. No. 07/803,834, allowed, discloses the one step synthesis of MTBE from t-butanol using hydrogen fluoride-modified montmorillonite clay catalysts.

In Ser. No. 07/878,121 there is described a haloacid-modified montmorillonite clay catalyst for producing MTBE from t-butanol and methanol.

With the current interest in the production of MTBE as a blending component in high octane gasoline, the identification of novel catalysts which provide substantial yields is important in the art. If a catalyst provides substantial yields of MTBE, permits the production in one step and incorporates the added feature of phase separation of the product above a certain temperature, such a catalyst represents a substantial advance in the art.

It would be a substantial advance in the art if methyl tertiary butyl ether could be selectively synthesized from tertiary butyl alcohol and methanol in one step using a catalyst which allows for rapid conversion of t-butanol. It has now been discovered that fluorophosphoric acid-modified Y-zeolites can be used as catalysts for the selective synthesis of methyl tertiary butyl ether from tertiary butyl alcohol and methanol. The accompanying examples demonstrate a significant improvement in yield of MTBE using the modified Y-type zeolites of the instant invention.

SUMMARY OF THE INVENTION

In accordance with certain of its aspects, the novel method of this invention for preparing methyl tert-butyl ether from tertiary butyl alcohol (t-butanol) and methanol in one-step comprises reacting tertiary butyl alcohol and methanol in the presence of a catalyst comprising a phosphoric acid-modified zeolite at an elevated temperature and moderate pressure. Examples demonstrate particularly the effectiveness of fluorophosphoric acid-modified Y-zeolites.

DESCRIPTION OF THE INVENTION

Preparation of the product of this invention may be carried out typically by reacting tertiary butyl alcohol and methanol in the presence of an etherification catalyst. The etherification is carried out in one step and the catalyst preferably comprises a Y-zeolite modified with a fluorophosphoric acid.

The reaction can be represented by the following:

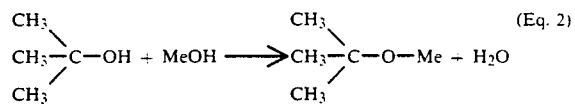

Generally the methanol and t-butanol coreactants may be mixed in any proportion in order to generate the desired methyl t-butyl ether, but preferably the molar ratio of methanol to t-butanol in the feed mixture should be between 10:1 and 1:10, if the yield of desired MTBE is to be maximized. In order to achieve maximum selectivity to MTBE, and optimum conversion per pass, an excess of methanol in the liquid feed is desirable. The most preferred methanol-to-tertiary butanol molar ratio is from 1:1 to 5:1.

In certain circumstances, it may be particularly desirable that the TBA conversion be high enough (e.g. >80% per pass), such that the crude product mix phase separates into an isobutylene-MTBE product-rich phase and a heavier aqueous methanol phase. Preferably such a product phase separation would be achieved at as low an etherification temperature as possible, but particularly in the range 160°-200° C.

The same process may also be applied to the preparation of other alkyl tertiary alkyl ethers. For example, said process may be applied to the reaction of a $C_1$–$C_6$ primary alcohol such as methanol, ethanol, n-propanol and n-hexanol with a $C_4$–$C_{10}$ tertiary alcohol such as, for example, tertiary butanol and tertiary amyl alcohol. Reaction of methanol with tertiary amyl alcohol (2-methyl-2-butanol) would then yield methyl tertiary amyl ether (TAME). Alternatively a mixture of alcohols, e.g., a mixture of $C_1$–$C_5$ alcohols, could be reacted to give a mixture of alkyl tert-alkyl ethers.

Good results were realized using certain crystalline aluminosilicate zeolites as catalysts for the reaction in Eq. 2, particularly the isostructural group of faujasite zeolites that include the synthetic Y-zeolites. The preferred Y-zeolites are the rare earth exchanged Y-zeolites.

The unit cells of zeolites are cubic, $a_o \approx 2.5$ nm, and each contains 192 silicon- or aluminum-centered oxygen tetrahedra which are linked through shared oxygen atoms. Because of the net negative charge on each of the aluminum-centered tetrahedra, each unit cell contains an equivalent number of charge-balancing cations. These are exclusively sodium ions in zeolites in their synthesized form. Typical cell contents for the Y-zeolites in the hydrated form are:

Y-zeolites are distinguished on the basis of the relative concentration of silicon and aluminum atoms and the consequent effects on detailed structure and related chemical and physical properties. The aluminum atoms in the unit cell of Y-zeolite vary from 76 to 48 giving a Si:Al ratio between 1.5 and 3.0. Both the cation concentration and charge density on the aluminosilicate structure are lower for Y-zeolites than for X-zeolites, where the aluminum atoms in the unit cell vary from 96 to 77.

The feature which determines the difference between faujasites and other zeolites built up from sodalite units is the double 6-membered ring or hexagonal prism, by which the units are linked. The sodalite unit, or β-cage, can be represented by a truncated octahedron, with the 24 silicon or aluminum atoms (designated T atoms)

taking positions at the vertices. The 36 oxygen atoms are displaced from the midpoints of the edges joining the vertices in order to attain tetrahedral configuration around the T atoms. The free diameter of the void within the β-cage is 0.66 nm, but only the smallest molecules can enter through the 0.22 nm diameter opening in the distorted ring of six oxygen atoms associated with each hexagonal face. Each sodalite unit is linked tetrahedrally across hexagonal faces by six bridging oxygens to four other sodalite units. The larger void spaces enclosed by sodalite units and hexagonal prisms are termed α-cages, or supercages. The α-cage is a 26-hedron with a free diameter of ≈1.3 nm, and it can be entered through four distorted 12-member rings of diameter 0.80–0.90 nm. In this way each α-cage is tetrahedrally joined to four others giving a complex system of void space extending throughout the zeolite structure. The α- and β-cages together give Y-zeolites, along with X-zeolites, the largest void volume of any known zeolites, which is ca. 50 vol % of the dehydrated crystal. From the catalytic viewpoint, the α-cages are by far the most important, since, unlike the β-cages, they permit entry of numerous aliphatic and aromatic compounds.

Particularly effective in the subject synthesis of MTBE are the synthetic Y-zeolites. Preferably said zeolites should be in an acidic form whereby some, or all, of the cations (Group I or II, alkali or alkaline earth metal ions such as sodium, potassium, calcium or magnesium) are exchanged by protons either through ammonium exchange followed by thermal stabilization (deammoniation, removal of $NH_3$) at elevated temperatures (e.g. 400°–500° C.), through mineral acid treatment, etc. Alternatively, said Y-zeolites may be dealuminized by hydrothermal treatment, by mineral acid treatment, or by treatment with ethylenediaminetetraacetic acid (EDTA) or other chelating agents, in which case said dealuminized Y-zeolites should have a Si:Al ratio of greater than three. A further possibility is that said Y-zeolites may be rare-earth exchanged with, for example, a mixture of rare-earth salts, by treatment with lanthanum salts, etc. Said rare-earth exchanged Y-zeolites would then have a Si:Al ratio of 1.5 to 3. The exchange of the sodium ions of the Y-zeolite by rare earth ions has been reviewed (see, for example, R. Rudham and A. Stockwell, The Chemical Society Specialist Periodical Report—Catalysis, Vol. I, 1977, Chapter 3).

Said catalysts may be in the form of powders, pellets, granules, spheres, shapes and extrudates. The examples described herein demonstrate the advantages of using extrudates. Illustrative of suitable zeolites which can be modified with fluorophosphoric acid or difluorophosphoric acid for the one-step synthesis of MTBE from methanol plus t-butanol include typical Y-type zeolites, particularly the rare-earth exchanged zeolites such as the Linde SK-500 extrudates, having a Si:Al ratio of between 1.5:1 and 2:1. As will be demonstrated by the examples, these catalysts are preferably of high purity and high surface area (i.e. >100 m²/g). The acid useful for modifying the Y-type zeolite is an acid from the group consisting of fluorophosphoric acid and its congeners. Fluorophosphoric acids useful for modifying the zeolites described SUPRA are selected from the group consisting of monofluorophosphoric acid [$O=P(OH)_2F$] difluorophosphoric acid [$O=P(OH)F_2$] and hexafluorophosphoric acid ($HPF_6$), in addition to phosphoric acid ($H_3PO_4$).

Good results were observed using difluorophosphoric acid, as demonstrated in Ex. 4 and Table 5. Example 2 and Table I demonstrate good results using fluorophosphoric acid.

Preparation of the fluorophosphoric acid-modified zeolite is accomplished by adding a solution of the fluorophosphoric acid in distilled water, or in an organic solvent, such as acetone, to the zeolite which is preferably in the form of an extrudate. The mixture is then stirred (or let stand) for from about 1 to 48 hours, under a nitrogen blanket, washed with distilled water and/or an appropriate organic solvent, and dried in vacuo at from about 20° to 100° C., followed by 20° to 300° C. Said fluorophosphoric acid-modified zeolites generally have titratable acidities up to 1 meq/g or higher.

The reaction may be carried out in either a stirred slurry reactor or in a fixed bed continuous flow reactor. The catalyst concentration should be sufficient to provide the desired catalytic effect.

Etherification can generally be conducted at temperatures from 20° to 250° C.; the preferred range is 80° to 200° C. The total operating pressure may be from 0 to 1000 psig, or higher. The preferred pressure range is 50 to 500 psig.

Typically, MTBE is generated continuously in up to ca. 30 wt % concentration in the crude liquid product at total liquid hourly space velocities (LHSV) of up to 6 or higher and relatively mild conditions, where:

$$LHSV = \frac{\text{Volume Of Total Liquid Feed Run Through The Reactor Per Hour}}{\text{Volume of Catalyst In Reactor}}$$

The examples which follow illustrate the one-step synthesis of MTBE from TBA and MeOH (Eq. 2) using Y-type zeolites particularly the form of high surface area extrudates, having fluorophosphoric acids deposited thereon. The examples are only intended as a means of illustration and it is understood the invention is not meant to be limited thereby.

Conversions of t-butanol (TBA, wt %) are estimated in the following examples using the equation:

$$\frac{(\text{Wt \% Conc. of TBA in Feed} - \text{Wt \% Conc. of TBA in Product})}{\text{Wt \% Conc. of TBA in Feed}} \times 100$$

Selectivities of methyl t-butyl ether (MTBE, mole %) and isobutylene ($C_4H_8$, mole %) are estimated from:

$$\frac{\text{Moles of MTBE (or } C_4H_8 \text{) in Product}}{\text{moles of TBA converted}} \times 100$$

Comparing the results of Examples 1–4 and comparative Examples A–C it may be noted that:

The performances in Examples 2 and 4 for the fluorophosphoric acid and difluorophosphoric acid-treated Y-zeolites, prepared by the methods of Examples 1 and 3, in comparison with the untreated Y-zeolites of comparative Example A and the fluorophosphoric and difluorophosphoric acid-treated X-zeolites of Examples B and C, show:

a. The TBA conversion levels with the fluorophosphoric acid and difluorophosphoric acid-treated Y-zeolites (Tables 1 and 5) at all operating temperatures are notably higher than for the untreated zeolite (Example A, Table 2) and for the fluorophosphoric acid treated X-zeolites (Examples B and C, Tables 3 and 4).

b. Only the fluorophosphoric and difluorophosphoric acid-treated Y-zeolites of Examples 2 and 4 achieve product phase separation into an isobutylene-MTBE rich phase and a heavier aqueous methanol phase (at 180° C. operating temperature).

EXAMPLE 1

This example illustrates the preparation of a fluorophosphoric acid-treated Y-zeolite.

To 500 cc of sample of Y-zeolite (LZY-52, from United Oil Products, 1/16" diameter extrudates, silica/alumina ratio 3.2, surface area 825 m$^2$/g, unit cell size 24.68Å) was added a solution of fluorophosphoric acid (10%) in distilled water in sufficient quantity to cover all the extrudates. The mix was allowed to stand for 1 hour, excess water removed by rotary evaporation, and the residual solids dried at 200° C., overnight.

The recovered white extrudates were found to comprise, by analysis:

| | |
|---|---|
| Phosphorus content | 3.7% |
| Water content | 0.96% |
| Acidity | 1.77 mg KOH/g or 0.03 meq/g |

EXAMPLE 2

This example illustrates the production of methyl t-butyl ether from t-butanol and methanol using the fluorophosphoric acid-treated Y-zeolite catalyst of Example 1.

Synthesis was conducted in a tubular reactor (½" id, 12" long) constructed of 316 stainless steel, operated upflow and mounted in a furnace, controllable to ±1.0° C. and fitted with pumps allowing flow control to <±1 cc/hr. The reactor was also fitted with a pressure regulating device and equipment for monitoring temperature, pressure and flow rate.

The reactor was charged at the beginning of the experiment with 25 cc of a sample of fluorophosphoric acid-treated LZY-52 zeolite, 1/16" diameter extrudates, prepared by the procedures of Example 1 and having an acid capacity of 1.77 mg KOH/g. A screen of glass wool was placed at the top and bottom of the reactor to ensure the catalyst would remain in the middle portion.

The catalyst bed was treated with a methanol/t-butanol (1.1:1 molar mix) upflow, at a flow rate of 50 cc/hr, while the reactor was held at 120° C., with a total pressure of 300 psi. Samples of crude product effluent were collected periodically on-stream, in 316 ss bombs and analyzed by glc and gc-ir.

Typical analyses data for samples taken under these conditions are summarized in Table 1. Performance at a series of other temperatures (140°, 160°, 180° C.) was determined using the same procedures. These results are also summarized in Table 1.

Of note, conversion levels and isobutylene/MTBE selectivities at 140°, 160° and 180° C. are as follows:

| Sample | Operating Temp (°C.) | tBA Conv. (%) | Molar Selectivity (%) | |
|---|---|---|---|---|
| | | | C$_4$H$_8$ | MTBE |
| 3 | 140 | 49 | 36 | 59 |
| 5 | 160 | 66 | 49 | 46 |
| 8 | 180 | 86 | a | a |

$^a$Not determined

TABLE I

MTBE/ISOBUTYLENE SYNTHESIS

| Ex. | Catalyst | MeOH/tBA Molar Ratio | Feed Rate (cc/hr) | Temp. (°C.) | Time On Stream (Days) | SAMPLE | PRODUCT COMPOSITION (WT %) | | | | |
|---|---|---|---|---|---|---|---|---|---|---|---|
| | | | | | | | H$_2$O | MeOH | C$_4$H$_8$ | tBA | MTBE |
| 2 | Ex. 1 | 1.1:1 | 50 | | | FS-1 | | 31.3 | | 68.5 | |
| | | | | 120 | 1 | 1 | 5.6 | 25.7 | 5.5 | 46.1 | 16.9 |
| | | | | | | 2 | 5.5 | 26.0 | 5.4 | 46.8 | 16.2 |
| | | | | 140 | 2 | →3 | 8.7 | 23.5 | 9.1 | 34.7 | 23.7 |
| | | | | | | 4 | 8.5 | 23.5 | 9.0 | 35.3 | 23.4 |
| | | | | 160 | 3 | →5 | 11.8 | 23.4 | 16.6 | 23.3 | 24.6 |
| | | | | | | 6 | 11.7 | 23.4 | 16.3 | 23.7 | 24.7 |
| | | | | 180 | 4 | 7 { 4.5 | 14.8 | 41.8 | 8.7 | 30.0 |
| | | | | | | { 35.0 | 42.1 | 4.3 | 9.2 | 9.0 |
| | | | | | | →8 { 5.0 | 15.7 | 39.7 | 9.5 | 29.9 |
| | | | | | | { 35.1 | 41.2 | 4.3 | 9.5 | 9.6 |

COMPARATIVE EXAMPLE A

This comparative example illustrates the performance of unmodified Y-zeolite (LZY-52) in the production of methyl t-butyl ether from t-butanol and methanol.

Using the equipment and procedures of Example 2, 25 cc of untreated Y-zeolite (LZY-52, United Oil Products, 1/16" E) was charged to the reactor system and performance was monitored over a series of temperatures (120°, 140°, 160°, 180° C.). The tBA/MeOH (1:1.1) feed rate was maintained at 50 cc/hr. The results are summarized in Table 2.

Calculated tBA conversions and C$_4$H$_8$/MTBE selectivities are as follows:

| Sample | Operating Temp (°C.) | tBA Conv. (%) | Molar Selectivity (%) | |
|---|---|---|---|---|
| | | | C$_4$H$_8$ | MTBE |
| 3 | 140 | 7.6 | a | a |
| 5 | 160 | 16 | a | a |
| 7 | 180 | 44 | 55 | 44 |

$^a$Not determined

TABLE 2

MTBE/ISOBUTYLENE SYNTHESIS

| Ex. | Catalyst | MeOH/tBA Molar Ratio | Feed Rate (cc/hr) | Temp. (°C.) | Time On Stream (Days) | SAMPLE | H$_2$O | MeOH | C$_4$H$_8$ | tBA | MTB |
|---|---|---|---|---|---|---|---|---|---|---|---|
| A | LZY-52 | 1.1:1 | 50 | | | FS-1 | | 31.1 | | 67.5 | |
| | | | | 120 | 1 | 1 | 1.3 | 29.6 | 1.8 | 62.0 | 5.0 |
| | | | | | | 2 | 1.3 | 30.2 | 1.6 | 63.1 | 3.5 |
| | | | | 140 | 2 | →3 | 1.4 | 30.1 | 2.0 | 62.4 | 3.8 |
| | | | | | | 4 | 1.3 | 29.1 | 1.7 | 62.9 | 3.8 |
| | | | | 160 | 3 | →5 | 3.0 | 28.7 | 4.1 | 56.7 | 7.2 |
| | | | | | | 6 | 2.5 | 29.4 | 3.6 | 57.0 | 6.2 |
| | | | | 180 | 4 | →7 | 7.8 | 26.2 | 12.3 | 37.7 | 15.6 |
| | | | | | | 8 | 7.2 | 26.0 | 11.9 | 39.2 | 15.4 |

COMPARATIVE EXAMPLE B

This comparative example illustrates the performance of a fluorophosphoric acid-treated X-zeolite in the production of methyl t-butyl ether from t-butanol and methanol.

Using the equipment and procedures of Example 2, 25 cc of a fluorophosphoric acid-treated 13 X-zeolite, prepared by a procedure similar to Example 1, was charged to the reactor system and performance was monitored over a series of temperatures (120°, 140°, 160°, 180° C.). The tBA/MeOH (1:1.1) feed rate was maintained at 50 cc/hr. The results are summarized in Table 3.

Calculated tBA conversion did not exceed 3% per pass throughout this temperature scan.

TABLE 3

MTBE/ISOBUTYLENE SYNTHESIS

| Ex. | Catalyst | MeOH/tBA Molar Ratio | Feed Rate (cc/hr) | Temp. (°C.) | Time On Stream (Days) | SAMPLE | H$_2$O | MeOH | C$_4$H$_8$ | tBA | MTBE |
|---|---|---|---|---|---|---|---|---|---|---|---|
| B | FP/13X$^a$ | 1.1:1 | 50 | | | FS-1 | | 31.2 | | 68.5 | |
| | | | | 120 | 1 | 1 | 0.1 | 30.6 | 0.1 | 69.0 | |
| | | | | | | 2 | 0.2 | 30.6 | 0.1 | 68.8 | |
| | | | | 140 | 2 | 3 | 0.1 | 30.5 | 0.1 | 69.0 | |
| | | | | | | 4 | 0.3 | 30.5 | 0.1 | 68.8 | |
| | | | | 160 | 3 | 5 | 0.2 | 30.5 | 0.2 | 68.8 | |
| | | | | | | 6 | 0.3 | 30.3 | 0.3 | 68.7 | |
| | | | | 180 | 4 | 7 | 0.5 | 30.3 | 1.1 | 66.5 | 1.2 |
| | | | | | | 8 | 0.6 | 30.4 | 1.0 | 66.5 | 1.1 |

$^a$Fluorophosphoric acid on 13X

COMPARATIVE EXAMPLE C

This comparative example illustrates the performance of a difluorophosphoric acid-treated X-zeolite in the production of methyl t-butyl ether from t-butanol and methanol.

Using the equipment and procedures of Example 2, 25 cc of a difluorophosphoric acid-treated 13 X-zeolite, prepared by a procedure similar to Example 1, was charged to the reactor system and performance was monitored over a series of temperatures (120°, 140°, 160°, 180° C.). The tBA/MeOH (1:1.1) feed rate was maintained at 50 cc/hr. The results are summarized in Table 4.

Calculated tBA conversions and C$_4$H$_8$/MTBE selectivities are as follows:

| Sample | Operating Temp (°C.) | tBA Conv. (%) | Molar Selectivity (%) C$_4$H$_8$ | MTBE |
|---|---|---|---|---|
| 3 | 140 | 1.3 | $a$ | $a$ |
| 6 | 160 | 6.7 | $a$ | $a$ |
| 7 | 180 | 25 | 48 | 52 |

$^a$Not determined

TABLE 4

MTBE/ISOBUTYLENE SYNTHESIS

| Ex. | Catalyst | MeOH/tBA Molar Ratio | Feed Rate (cc/hr) | Temp. (°C.) | Time On Stream (Days) | SAMPLE | H$_2$O | MeOH | C$_4$H$_8$ | tBA | MTBE |
|---|---|---|---|---|---|---|---|---|---|---|---|
| C | F$_2$P/13X$^a$ | 1.1:1 | 50 | | | FS-1 | | 31.3 | | 68.4 | |
| | | | | 120 | 1 | 1 | 0.4 | 30.4 | 0.2 | 68.8 | |
| | | | | | | 2 | 0.3 | 30.5 | 0.1 | 68.7 | |
| | | | | 140 | 2 | →3 | 0.4 | 30.4 | 0.4 | 67.5 | 1.0 |
| | | | | | | 4 | 0.4 | 30.4 | 0.4 | 67.6 | 0.9 |
| | | | | 160 | 3 | 5 | 1.2 | 29.6 | 1.4 | 64.0 | 3.5 |
| | | | | | | →6 | 1.2 | 29.8 | 1.5 | 63.8 | 3.3 |
| | | | | 180 | 4 | →7 | 4.2 | 27.6 | 6.1 | 51.4 | 10.4 |

TABLE 4-continued

MTBE/ISOBUTYLENE SYNTHESIS

| Ex. | Catalyst | MeOH/tBA Molar Ratio | Feed Rate (cc/hr) | Temp. (°C.) | Time On Stream (Days) | PRODUCT COMPOSITION (WT %) | | | | | |
|---|---|---|---|---|---|---|---|---|---|---|---|
| | | | | | | SAMPLE | H₂O | MeOH | C₄H₈ | tBA | MTBE |
| | | | | | | 8 | 4.1 | 27.8 | 5.6 | 52.7 | 9.4 |

$^a$Difluorophosphoric acid on 13X

EXAMPLE 3

This example illustrates the preparation of a difluorophosphoric acid-treated Y-zeolite.

Following the procedures of Example 1, a sample of Y-zeolite (LZY-52) was treated with difluorophosphoric acid (10%) aqueous solution and the mixture allowed to stand for 1 hour. After removal of the excess water by rotary evaporation and drying at 200° C., overnight, the recovered white extrudates were found to comprise, by analyses:

| Phosphorus content | 4.1% |
|---|---|
| Water content | 0.33% |
| Acidity | 2.61 mg KOH/g or 0.05 meq/g |

EXAMPLE 4

This example illustrates the performance of a difluorophosphoric acid-modified Y-zeolite in the production of methyl t-butyl ether from t-butanol and methanol.

Using the equipment and procedures of Example 2, 25 cc of the difluorophosphoric acid-treated LZY-52 of Example 3 was charged to the reactor system and performance was monitored over a series of temperatures (120°, 140°, 160°, 180° C.). The tBA/MeOH 1:1.1) feed rate was maintained at 50 cc/hr. The results are summarized in Table 5.

Calculated tBA conversions and C₄C₈/MTBE selectivities are as follows:

| Sample | Operating Temp (°C.) | tBA Conv. (%) | Molar Selectivity (%) | |
|---|---|---|---|---|
| | | | C₄H₈ | MTBE |
| 3 | 140 | 50 | 36 | 61 |
| 5 | 160 | 63 | 50 | 46 |
| 7 | 180 | 87 | $^a$ | $^a$ |

$^a$Not determined

TABLE 5

MTBE/ISOBUTYLENE SYNTHESIS

| Ex. | Catalyst | MeOH/tBA Molar Ratio | Feed Rate (cc/hr) | Temp. (°C.) | Time On Stream (Days) | PRODUCT COMPOSITION (WT %) | | | | | |
|---|---|---|---|---|---|---|---|---|---|---|---|
| | | | | | | SAMPLE | H₂O | MeOH | C₄H₈ | tBA | MTBE |
| 4 | Ex. 3 | 1.1:1 | 50 | | | FS-1 | | 31.4 | | 68.4 | |
| | | | | 120 | 1 | 1 | 5.4 | 25.2 | 5.4 | 46.3 | 17.4 |
| | | | | | | 2 | 5.4 | 25.3 | 5.4 | 46.5 | 17.2 |
| | | | | 140 | 2 | →3 | 8.7 | 22.7 | 9.2 | 34.4 | 24.8 |
| | | | | | | 4 | 8.8 | 22.8 | 9.0 | 34.7 | 24.4 |
| | | | | 160 | 3 | →5 | 11.3 | 23.3 | 16.3 | 25.5 | 23.3 |
| | | | | | | 6 | 11.5 | 23.9 | 15.6 | 26.7 | 22.1 |
| | | | | 180 | 4 | →7 { 4.3 | 14.3 | 43.4 | 8.2 | 29.5 | |
| | | | | | | { 35.1 | 42.0 | 4.3 | 8.9 | 8.9 | |
| | | | | | | 8 { 4.8 | 14.9 | 42.1 | 8.5 | 29.4 | |
| | | | | | | { 35.1 | 42.0 | 4.4 | 9.1 | 9.0 | |

What is claimed is:

1. In a method wherein t-butanol is reacted with methanol in a one step in the presence of a catalyst to provide methyl tert-butyl ether, the improvement of using as a catalyst a crystalline aluminosilicate faujasite-type Y-zeolite modified with a fluorophosphoric acid and continuously contacting said t-butanol and methanol in a molar amount of about 0.1 to 10 moles of methanol per mole of t-butanol with said catalyst at a temperature of about 20° C. to about 250° C. and a pressure of about atmospheric to about 1000 psig to obtain methyl tert-butyl ether product.

2. The method of claim 1 wherein the fluorophosphoric acid is selected from the group consisting of monofluorophosphoric acid [O=P(OH)₂F], difluorophosphoric acid [O=P(OH)F₂] and hexafluorophosphoric acid (HPF₆).

3. The method of claim 1 wherein the acid is selected from the group consisting of monofluorophosphoric acid and difluorophosphoric acid.

4. The method of claim 1 wherein the Y-zeolite is rare-earth exchanged.

5. The method of claim 1 wherein said fluorophosphoric acid-treated Y-zeolite has a titratable acidity of up to 1 meq/g or higher.

6. The method of claim 1 wherein the Y-zeolite catalyst has a surface of greater than 100 m²/g.

7. The method of claim 1 wherein the temperature is from about 80° C. to about 200° C.

8. The method of claim 1 wherein the operating temperature is in the range 160° to 200° C. and the product comprises a two-phase mix of an isobutylene-methyl tert-butyl ether product-rich phase and a heavier aqueous methanol-rich phase.

* * * * *